United States Patent [19]

Chambers et al.

[11] Patent Number: 4,514,394

[45] Date of Patent: Apr. 30, 1985

[54] ANTI-HYPERTENSIVE USE OF 1-(4'-BRANCHED ALKYLSULFONYLPHENYL)-6-CHLORO-7,8-DIHYDROXY-2,3,4,5-TETRAHYDRO-1H-3-BENZAZEPINES

[75] Inventors: Pamela A. Chambers, Wayne; Joseph Weinstock, Phoenixville, both of Pa.

[73] Assignee: Smithkline Beckman Corporation, Philadelphia, Pa.

[21] Appl. No.: 498,351

[22] Filed: May 25, 1983

[51] Int. Cl.³ .............................................. A61K 31/55
[52] U.S. Cl. .............................. 514/213; 260/239 BB
[58] Field of Search ................. 260/239 BB; 424/244

[56] References Cited

U.S. PATENT DOCUMENTS 4,104,379 8/1978 Gallagher, Jr. et al. ........... 424/244

Primary Examiner—Glennon H. Hollrah
Assistant Examiner—D. B. Springer
Attorney, Agent, or Firm—William H. Edgerton; Richard D. Foggio; Alan D. Lourie

[57] ABSTRACT

6-Chloro-7,8-dihydroxy-1-phenyl-2,3,4,5-tetrahydro-1H-3-benzazepines whose structures have an isopropylsulfonyl, isopropylthio, isobutylsulfonyl or isobutylthio group substituted at the 4-position of the 1-phenyl substituent have potent renal dopaminergic and anti-hypertensive activity.

7 Claims, No Drawings

ANTI-HYPERTENSIVE USE OF 1-(4'-BRANCHED ALKYLSULFONYLPHENYL)-6-CHLORO-7,8-DIHYDROXY-2,3,4,5-TETRAHYDRO-1H-3-BENZAZEPINES

This invention comprises certain 6-chloro-7,8-dihydroxy-1-phenyl-2,3,4,5-tetrahydro-1H-3-benzazepines which have been found to demonstrate unexpectedly potent dopaminergic activity. The benzazepine nucleus in the structures of these compounds is characterized by having two critical parameters, a 6-chloro substituent and a 1-phenyl substituent which has an isopropylsulfonyl, isopropylthio, isobutylsulfonyl or isobutylthio group specifically placed in the para position.

BACKGROUND OF THE INVENTION

U.S. Pat. No. 4,104,379 describes a generic group of 1-phenyl-2,3,4,5-tetrahydro-1H-3-benzazepines related to the present invention. More specifically, the patent at column 1, line 35 describes the structures of the compounds as having a "functional sulfur containing group such as lower alkylthio, sulfonyl or sulfinyl groups" substituted as a floating substituent on the 1-phenyl ring. Lower alkyl is defined to include "straight or branched alkyl groups having 1 to 5 carbon atoms". Preference is expressed for certain methylthio, sulfinyl or sulfonyl substituents at column 2 of the patent. The m-methylsulfonyl containing structures were also described as one of a group of species of note, column 2, structure II. No higher alkylsulfonyl or alkylthiophenyl containing structures are disclosed or exemplified in U.S. Pat. No. 4,104,379.

Moderate dopaminergic activities of selected species are described in the patent with $ED_{15}$ values of 40–130 µg/kg in the anesthetized renal dog protocol which is a test protocol used in this art to demonstrate dopaminergic activity.

DESCRIPTION OF THE INVENTION

The compounds of this invention are distinguished by structures which have a branched $C_{4-5}$-alkylsulfonyl or branched $C_{4-5}$-alkylthio substituent in the para position of the 1-phenyl ring of 6-chloro-7,8-dihydroxy-1-phenyl-2,3,4,5-tetrahydro-1H-3-benzazepine. These compounds have an unexpectedly potent effect in the renal protocol in the anesthetized dog ($ED_{15}$) which is mentioned above as well as in the spontaneously hypertensive rat (SHR) protocol which demonstrates anti-hypertensive activity. Generally speaking, this biological activity is 5–15 times greater than that of the corresponding straight chain congeners or of the methyl congeners despite the increase in weight and bulk of the branched chain groups in the latter comparison.

The compounds of this invention are illustrated by the structural formula:

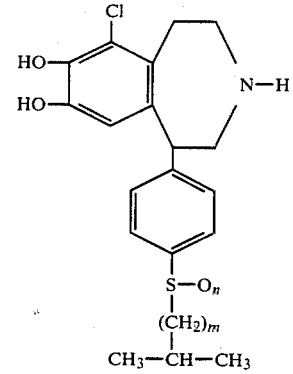

in which:

n is 0 or 2; and
m is 0 or 1.

Preferred compounds are those of formula I in which n is 2, i.e. the two sulfones.

Formula I represents four chemical compounds in the form of the bases. The pharmaceutically acceptable, acid addition salts of the bases are also included in this invention, for example, those prepared with hydrobromic, hydrochloric, sulfuric, phosphoric, acetic, sulfamic, methanesulfonic, ethanedisulfonic, succinic, maleic or fumaric acids. The salts are prepared by reacting the base with at least one equivalent of acid in an organic solvent, then, isolating the salt as known to the art.

Also included in this invention are the 7,8-di-$C_{2\text{-}6}$-alkanoyl ester prodrug derivatives, for example, the di-acetyl, di-isobutyryl, di-butyryl, di-isovaleryl or di-isopropionyl esters. These are prepared by reacting the selected base in a N-protected form, such as a salt or another easily removable group at the 3-position, with at least two equivalents of an acyl halide or anhydride.

It will be obvious to one skilled in the art that the compounds of formula I may be present as enantiomers which may be resolved into d or l optical isomers. Resolution of the optical isomers is conveniently accomplished by fractional crystallization of the salts which are formed by reacting the bases, or an ether derivative thereof, with optically active acids. Unless otherwise specified herein or in the claims, it is intended to include all isomers, whether separated or mixtures thereof.

The compounds of formula 1 are prepared by treating the 7,8-dimethoxy derivative with boron tribromide in methylene chloride in the cold. The desired end products are isolated from the reaction mixture by standard chemical procedures. The sulfone intermediates are prepared from their sulfide congeners by oxidation of the corresponding thio compound, for example using a perbenzoic acid, such as m-chloroperbenzoic acid, usually in methylene chloride at room temperature.

The sensitive N- or 3-position is protected from oxidation during sulfone formation as known in the art, for example, by inserting an easily removed trifluoroacetyl group or by making a salt with a strong acid. Details of the overall synthetic sequence are described in the examples.

The unusual nature of the biological properties of the compounds of this invention will be evident to one skilled in the art by comparing their activities with those of the 4'-methyl congeners or with the 4'-n-alkyl congeners having the same number of carbon atoms in the alkyl group. The data in the following table were determined using the renal-rigged anesthetized dog ($ED_{15}$), as described in detail in U.S. Pat. No. 4,104,379, and in the standard antihypertensive protocol in spontaneously hypertensive rats (SHR).

TABLE A

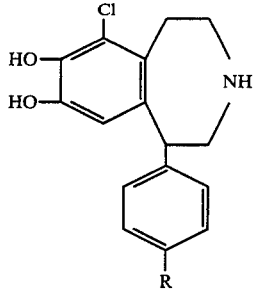

| Compound | $ED_{15}$ (μg/kg) | SHR (mg/kg)* | |
|---|---|---|---|
| A. $-SO_2CH(CH_3)_2$ | 3.0 | 12.5 | active |
| B. $-SO_2CH_2CH_2CH_3$ | 56 | 25 | active |
| C. $-SO_2CH_3$ | 77 | 25 | active |
| D. $-SO_2CH_2CH(CH_3)_2$ | 4.7 | 3.12 | active |
| E. $-SO_2CH_2CH_2CH_2CH_3$ | 25 | 50 | active |
| F. $-S-CH_2CH(CH_3)_2$ | 3.0 | 25 | active |
| G. $-S-CH_2CH_2CH_2CH_3$ | 30 (primary screen) | 50 | toxic |
| H. $-S-CH_3$ | 60 | — | |
| I. $3-SO_2CH(CH_2)_2$ | 7.7 | 50 | toxic |
| J. $3-SO_2CH_3$ | 11 | 25 | active |
| K. 6-F $-SO_2CH(CH_3)_2$ | inactive (RVR) at 3, 30, 300 | — | |
| L. 6-F $-SO_2CH_2CH(CH_3)_2$ | inactive (RVR) at 3, 30, 300 | — | |

*Minimal dose at which significant activity was observed at 3 hours post dose.

The data in Table A demonstrate the unusual increase in potency of the compounds whose structures have a higher, branched alkyl sulfonyl or thio substituent on the 1-phenyl ring. Also, the 3'-substitution of the isopropylsulfonyl gives a compound which demonstrated toxicity in the SHR test, for example, hematuria, convulsions and death. The compounds claimed, therefore, have from 3-25 times the potency in the $RVR-ED_{15}$ values compared with the respective compounds specifically described in U.S. Pat. No. 4,104,379 or with straight chain compounds. Also, the preferred species, Compound D, is very active as an antihypertensive in the SHR.

Finally, the compounds whose structures have the 4'-isopropyl or isobutylsulfonyl substituents in the 6-fluoro series have weak renal activity which indicates the importance of the 6-chloro substituent in structure-activity consideration of the compounds of this invention.

The pharmaceutical compositions of this invention having renal and anti-hypertensive activities are prepared in conventional dosage unit forms by incorporating a compound of formula I, an optical isomer, an O-alkanoyl derivative or a pharmaceutically acceptable acid addition salt thereof, with a nontoxic pharmaceutical carrier according to accepted procedures. The compounds of this invention are present in a nontoxic dosage unit amount sufficient to produce the desired pharmacodynamic activity safely in a subject, animal or human, in need of such treatment. Preferably the compositions contain the active ingredient in an active but nontoxic amount selected from about 25 mg to about 300 mg of active ingredient per dosage unit but this quantity depends on the specific biological activity desired and the conditions of patient. The compositions are administered as found necessary to maintain effective antihypertensive activity or to improve renal dysfunction, usually from 1-5 times daily.

The pharmaceutical carrier employed is, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may optionally include any time delay material well known to the art, such as glyceryl monostearate or glyceryl distearate alone or with a wax.

A wide variety of pharmaceutical forms are employed. Thus, if a solid carrier for oral administration is used the preparation is tableted, placed in a hard gelatin capsule in powder or pellet form, or in the form of a troche or lozenge. The amount of solid carrier varies widely but preferably is from about 25 mg to about 1 g. If a liquid carrier is used, the preparation is in the form of a syrup, emulsion, soft gelatin capsule, sterile injectable liquid such as an ampul or a liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing renal function improvement and anti-hypertensive activity in accordance with this invention comprises administering internally to a subject in need of such activity a compound of formula I or a pharmaceutically acceptable derivative thereof, usually combined with a pharmaceutical carrier, in a nontoxic amount sufficient to produce said activity as described above. The route of administration is any route which effectively transports the active compound to the dopamine receptors which are to be stimulated such as orally or parenterally, the oral route being preferred. Advantageously, equal doses are administered several times, such as two or four times, per day with the daily dosage regimen being selected from about 50 mg to about 1 g. When the method described above is carried out, renal dilating and anti-hypertensive activities are produced.

The following examples are designed solely to illustrate the preparation and use of the compounds of this invention. The temperatures are Centigrade. Other variations of these examples will be obvious to those skilled in the art.

EXAMPLE 1

A mixture of 12.49 (0.22 m) of potassium hydroxide and 150 ml of ethanol was mixed with 28.4 g (0.15 m) of 4-bromothiophenol and 33 g (20.7 ml, 0.18 ml) of isobutyl iodide. The mixture was heated at reflux for 5 hours, filtered and evaporated. Water was added to the residue. The mixture was extracted with ethyl acetate. The organic extract was washed with water, dried and evaporated to give 34.6 g of 4-bromophenylisobutylsulfide.

This compound, 34.6 (0.15 ml), was dissolved in 200 ml of ethyl ester and the solution cooled to −20° at which temperature 115 ml of a 1.3 m solution of n-butyllithium in hexane was added under nitrogen. After allowing the reaction mixture to warm to 10°, it was recooled to −10° when 50 ml of dimethylformamide was added dropwise. After stirring at 0° for 15 minutes, the mixture was poured into 500 ml of saturated ammonium chloride solution. The separated aqueous layer was washed with ether. The combined organic layers were washed with water, dried and evaporated to give 32.2 g of 4-isobutylthiobenzaldehyde.

The benzaldehyde (32.2 g, 0.15 ml), 37.6 g (0.185 m) of trimethylsulfonium iodide and 150 ml of dimethylsulfoxide was held at 20°–25° while a solution of 18.6 g (0.17 m) of potassium tert-butoxide and 100 ml of dimethylsulfoxide was added dropwise. After stirring at room temperature for 1 hour, the mixture was poured into water. The styrene oxide was extracted into ethyl acetate, then, recovered by drying and evaporating the extract, 26.5 g of p-isobutylthiostyrene oxide.

A mixture of 26.5 g (0.14 m) of the styrene oxide and 32 g (1.25 m) of chlorohomoveratryl amine was heated under nitrogen at 115° for 24 hours. The cooled melt was purified by chromatography over a silica gel column using a gradient methanol/methylene chloride elution system. The combined fractions which carry the secondary amine (TLC) were evaporated and the residual oil taken up in ether. N-[(2-Hydroxy-2-4'-isobutylthiophenyl)ethyl]-N-[2-(2'-chloro-3',4'-dimethoxyphenyl)ethyl]amine (9.2 g) was crystallized from ether solution, m.p. 80°–81°.

Anal. Calcd. for $C_{22}H_{30}ClNO_3S$: C, 62.32; H, 7.13; N, 3.30. Found: C, 62.46; H, 7.12; N, 3.44.

A mixture of 9.0 g (0.022 m) of the secondary amine, 3.1 ml of conc. sulfuric acid and 100 ml of trifluoroacetic acid was monitored by thin layer chromatography (TLC) over silica at 30 minute intervals to follow the course of the reaction. After 1 hour, the solvent was evaporated and ice added to the residue. The mixture was taken to pH 8 and extracted with ethyl acetate. The extract was washed with water, dried and evaporated to give 8.5 g of base, 6-chloro-1-(4'-isobutylthiophenyl)-7,8-dimethoxy-2,3,4,5-tetrahydro-1H-3-benzazepine.

The base (200 mg) was dissolved in ether and treated with an excess of ethereal hydrogen chloride to give the hydrochloride salt which was recrystallized from methanol/ethyl acetate, m.p. 124°–126°.

Anal. Calcd. for $C_{22}H_{28}ClNO_2S.HCl$: C, 59.73; H, 6.61; N, 3.17. Found: C, 59.63; H, 6.59; N, 3.25.

A mixture of 2.3 g (0.0054 m) of the benzazepine obtained above and 50 ml of dry methylene chloride was cooled to −15°. A mixture of 4.8 g (0.019 m) of boron tribromide and 30 ml of dry methylene chloride was added dropwise under nitrogen. The reaction was allowed to stir at room temperature for 30 minutes, then, cooled to 0°. Methanol was added to decompose excess tribromide. The solvents were stripped. The residue was dissolved in methanol and the solution evaporated again. The residue was recrystallized from methanol/acetonitrile to give 1.4 g of 6-chloro-1-(4'-isobutylthiophenyl)-7,8-dihydroxy-2,3,4,5-tetrahydro-1H-3-benzazepine hydrobromide, m.p. 229°–231°.

Anal. (NMR shows partial acetonitrile solvate) Calcd. for $C_{20}H_{24}ClNO_2S.HBr$: C, 52.35; H, 5.49; N, 3.05. Found: C, 52.38, 52.25; H, 5.53, 5.57.

EXAMPLE 2

A mixture of 6.0 g (0.015 m) of 6-chloro-1-(4'-isobutylthiophenyl-7,8-dimethoxy-2,3,4,5-tetrahydro-1H-3-benzazepine, 10 ml (0.071 m) of trifluoroacetic anhydride and 100 ml of methylene chloride was stirred for 2 hours and allowed to stand for 2 days. The reaction mixture was carefully shaken with several portions of 5% sodium bicarbonate solution. IR and NMR spectral analysis confirmed N-acylation.

The solution (0.015 mol of benzazepine) was added to a mixture of 8.0 g (0.038 m) of m-chloroperbenzoic acid and 50 ml of methylene chloride at −10°. After stirring at room temperature for 3 hours, the mixture was shaken with several portions of bicarbonate solution, washed with water and dried to give 8.9 g of 6-chloro-1-(4'-isobutylsulfonylphenyl)-7,8-dimethoxy-3-trifluoroacetyl-2,3,4,5-tetrahydro-1H-3-benzazepine.

A mixture of 8.9 g (0.015 m) of the amide, 1 g (0.025 m) of sodium hydroxide and 100 ml of methanol was stirred at room temperature for 2 hours, then, poured into water. The quench was extracted with ethyl acetate. The extract was washed with water, dried and evaporated to give 4.4 g of 6-chloro-1-(4'-isobutylsulfonylphenyl)-7,8-dimethoxy-2,3,4,5-tetrahydro-1H-3-benzazepine.

This base (1 g) was treated with methanol/ethereal hydrogen chloride to give the hydrochloride salt, from methanol/ethyl acetate; m.p. 233°–236°.

Anal. Calcd. for $C_{22}H_{28}ClNO_4S.HCl$: C, 55.70; H, 6.16; N, 2.95. Found: C, 55.33; H, 6.32; N, 3.24.

A mixture of 3.4 g (0.0078 m) of the dimethoxy benzazepine base and 60 ml of dry methylene chloride was cooled to −15° at which temperature a mixture of 6.4 g (2.6 ml, 0.027 m) of boron tribromide and 30 ml of methylene chloride was added under nitrogen. The mixture was stirred at room temperature for 30 minutes, then, cooled to 0° and methanol added. The solvents were evaporated. The residue was stripped from methanol several times. Trituration of the residue with acetonitrile gave a gummy powder which was taken through methanol/acetonitrile to give 1.97 g of 6-chloro-1-(4'-isobutylsulfonyl)-7,8-dihydroxy-2,3,4,5-tetrahydro-1H-3-benzazepine hydrobromide, m.p. 178°–180°.

Anal. Calcd. for $C_{20}H_{24}ClNO_4S.HBr.0.75H_2O$: C, 47.63; H, 5.30; N, 2.78. Found: C, 47.56; 47.44; N, 4.98, 5.13; N, 3.11, 3.02. NMR, IR and TLC (Rf 0.80 checked).

The hydrobromide salt (750 mg) is shaken with an ether/carbonate mixture. The ether layer is removed, dried and divided into two aliquots. Evaporating one of these gave the base and saturating the other with dry hydrogen chloride gas gave the hydrochloride salt.

The product as the hydrobromide salt (150 mg) is mixed with 150 mg of lactose, filled into a gelatin capsule and administered orally to a hypertensive patient three times daily.

EXAMPLE 3

The reaction sequence of Example 1 was repeated using isopropyl iodide in the first step with the following new intermediates isolated:

N-[(2-hydroxy-2-4'-isopropylthiophenyl)ethyl]-N-[[2-(2'-chloro-3',4'-dimethoxyphenyl)ethyl]amine, m.p. 75°–76°.

Anal. Calcd. for $C_{21}H_{28}ClNO_3S$: C, 61.52; H, 6.88; N, 3.42. Found: C, 61.24, 60.81; H, 6.78, 6.87; N, 2.92, 3.03.

6-Chloro-7,8-dimethoxy-1-(4-isopropylthiophenyl)-2,3,4,5-tetrahydro-1H-3-benzazepine hydrochloride.

Anal. Calcd. for $C_{21}H_{26}ClNO_2S.HCl$: C, 58.59; H, 6.32; N, 3.25. Found: C, 56.87; H, 6.22; N, 3.08.

A mixture of 8.8 g (0.022 m) of the dimethoxy benzazepine, 100 ml of dry methylene chloride and 4 ml (0.03 m) of trifluoroacetic anhydride was reacted and worked up as above to give 10 g of the N-trifluoroacetylbenzazepine analyzed by NMR, IR and TLC.

This solid, 10 g (0.021 m), was dissolved in chloroform and added to a suspension of 10.5 g (0.052 m) of 85% m-chloroperbenzoic acid in 200 ml of chloroform at −10°. After warming to room temperature and stirring for 3 hours, the reaction mixture was shaken with several portions of 5% sodium bicarbonate solution, washed with water, dried and evaporated to give 13.6 g of the sulfone amide, Rf p=0.75, s=0.89 (silica, 10% methanol in methylene chloride).

This compound (13.6 g) along with 3 g (0.075 m) of sodium hydroxide in 100 ml of methanol was stirred at room temperature for 2 hours, then, poured into water. The quench was extracted with ethyl acetate. The extract was washed with water, dried and evaporated to give 8.1 g (95%) of 6-chloro-7,8-dimethoxy-1-(4'-isopropylsulfonylphenyl)-2,3,4,5-tetrahydro-1-3H-benzazepine.

A 2 g sample of the base was reacted in methylene chloride with ethereal hydrogen chloride to give 1.14 g of the hydrochloride salt from methanol/ether, m.p. 163°-165°.

Anal. Calcd. for $C_{21}H_{27}ClNO_4S \cdot HCl \cdot 0.5H_2O$: C, 53.62; H, 6.21; N, 2.98. Found: C, 54.00, 53.55; H, 6.22, 6.23; N, 3.01, 2.93.

A mixture of 6.4 g (0.015 m) of the dimethoxy base and 150 ml of dry methylene chloride was cooled to −10°, at which point, 13.6 g (0.052 m) of boron tribromide in 80 ml of methylene chloride was added. After stirring at room temperature for ½ hour, the mixture is cooled and methanol added. The solvents were evaporated. The residue was stripped from methanol to give 2.88 g of 6-chloro-7,8-dihydroxy-1-(4'-isopropylsulfonylphenyl)-2,3,4,5-tetrahydro-1-3H-benzazepine hydrobromide, which was recrystallized from methanol/acetonitrile, Rf 0.73 (63 methylene chloride/31 methanol/6 conc. ammonium hydroxide); m.p. 265°-266°.

Anal. Calcd. for $C_{19}H_{22}ClNO_4S \cdot HBr \cdot 0.25H_2O$: C, 47.41; H, 4.92; N, 2.91. Found: C, 47.35, 47.08; H, 4.98; 4.95; N, 3.03, 2.78.

This compound (75 mg) was mixed with lactose (200 g), filled into a hard gelatin capsule and given orally 4 times a day to a patient in need of improved renal function.

EXAMPLE 4

A mixture of 2.1 g (0.0054 m) of 6-chloro-7,8-dimethoxy-1-(4'-isopropylthiophenyl)-2,3,4,5-tetrahydro-1H-3-benzazepine from Example 3 and 50 ml of dry methylene chloride is reacted at −10° with 4.6 g (0.0186 m) of boron tribromide in 20 ml of methylene chloride. After working the reaction mixture up as described above, 1.2 g of 6-chloro-7,8-dihydroxy-1-(4'-isopropylthiophenyl)-2,3,4,5-tetrahydro-1H-3-benzazepine hydrobromide was recovered, m.p. 285°-286°.

Anal. Calcd. for $C_{19}H_{22}ClNO_2S \cdot HBr$: C, 51.30; H, 5.21, N, 3.15. Found: C, 51.65; H, 5.42; N, 3.34.

EXAMPLE 5

A mixture of 1.5 g of 6-chloro-1-(4'-isobutylsulfonylphenyl)-7,8-dihydroxy-2,3,4,5-tetrahydro-1H-3-benzazepine hydrobromide in 50 ml of trifluoroacetic acid is reacted with 15 ml of isobutyryl bromide at room temperature. After starting for 2 hours, addition of ether gives the desired 6-chloro-1-(4'-isobutylsulfonylphenyl)-7,8-di-isobutyryloxy-2,3,4,5-tetrahydro-1H-3-benzazepine hydrobromide.

Other 7,8-dialkanoyl derivatives are prepared in similar manner.

What is claimed is:

1. The method of inducing anti-hypertensive activity in a subject in need thereof comprising administering orally or parenterally to said subject an anti-hypertensively effective, nontoxic quantity of a compound of the structural formula:

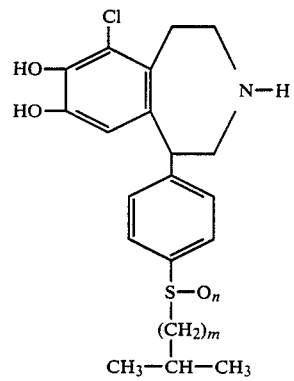

in which:
m is 0 or 1, and
n is 0 or 2, a pharmaceutically acceptable, acid addition salt or a di-$C_{2-6}$-alkanoyl ester derivative thereof.

2. The method of claim 1 in which the compound is 6-chloro-7,8-dihydroxy-1-(4'-isobutylsulfonylphenyl)-2,3,4,5-tetrahydro-1H-3-benzazepine.

3. The method of claim 1 in which the compound is 6-chloro-7,8-dihydroxy-1-(4'-isobutylsulfonylphenyl)-2,3,4,5-tetrahydro-1H-3-benzazepine hydrochloride.

4. The method of claim 1 in which the compound is 6-chloro-7,8-dihydroxy-1-(4'-isopropylsulfonylphenyl)-2,3,4,5-tetrahydro-1H-3-benzazepine.

5. The method of claim 1 in which the compound is 6-chloro-1-(4'-isobutylthiophenyl)-7,8-dihydroxy-2,3,4,5-tetrahydro-1H-3-benzazepine.

6. The method of claim 1 in which the compound is 6-chloro-7,8-dihydroxy-1-(4'-isopropylthiophenyl-2,3,4,5-tetrahydro-1H-3-benzazepine.

7. The method of claim 1 in which the quantity of compound is selected from the range of from 25-300 mg per dosage unit and is administered from 1-5 times daily.

* * * * *